(12) United States Patent
Cines et al.

(10) Patent No.: US 7,576,060 B2
(45) Date of Patent: Aug. 18, 2009

(54) INHIBITION OF ADHESION AND MIGRATION OF AN ENDOTHELIAL CELL TO FIBRONECTIN BY NEUTROPHIL ALPHA-DEFENSINS

(75) Inventors: Douglas Cines, Wynnewood, PA (US); Khalil Bdeir, Jenkintown, PA (US); Triantafyllos Chavakis, Chevy Chase, MD (US); Klaus T. Preissner, Giessen (DE)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 183 days.

(21) Appl. No.: 11/185,626

(22) Filed: Jul. 20, 2005

(65) Prior Publication Data

US 2006/0074020 A1    Apr. 6, 2006

Related U.S. Application Data

(63) Continuation of application No. 10/983,527, filed on Nov. 8, 2004, now abandoned.

(60) Provisional application No. 60/518,443, filed on Nov. 7, 2003.

(51) Int. Cl.
*A61K 38/17* (2006.01)
(52) U.S. Cl. ...................................................... 514/12
(58) Field of Classification Search ........................ None
See application file for complete search history.

(56) References Cited

OTHER PUBLICATIONS

Bdeir et al., Inhibition of neovascularization by alpha defensins: a potential link between inflammation and angiogenesis, 2002, Blood, Nov. 16, vol. 100, Issue, Abstract No. 2673.*

Chavakis et al., Regulation of neovascularization by human neurophil peptides (alpha-defensisn): a link between inflammation and angiogenesis, 2004, FASEB Journal Express, online publication Jun. 18.*

Chavakis et al.,Regulation of neovascularization by human neurophil peptides (alpha-defensins): a link between inflammation and angiogenesis, 2004, FASEB Journal Express, vol. 18, Issue 11, pp. 1306-1308.*

Brodgen et al., Defensin-induced adaptive immunity in mice and its potential in preventing periodontal disease, Apr. 2003, vol. 18, Issue 2, pp. 95-99.*

Chaly et al. European Cytokine Network, Jun. 2000, vol. 11, No. 2, pp. 257-266.*

Harwig et al., "Neutrophil Defensins: Purification, Characterization, and Antimicrobial Testing," *Methods in Enzymology*, vol. 236, pp. 160-172, 1994.

Higazi et al., "Defensin Modulates Tissue-Type Plasminogen Activator and Plasminogen Binding to Fibrin and Endothelial Cells," *The Journal of Biological Chemistry*, vol. 271, pp. 17650-17655, 1996.

Higazi et al., "Defensin Stimulates the Binding of Lipoprotein (a) to Human Vascular Endothelial and Smooth Muscle Cells," *Blood*, vol. 12, pp. 4290-4298, 1997.

Zhou et al., "Impaired Angiogenesis, Delayed Wound Healing and Retarded Tumor Growth in Perlecan Heparan Sulfate-Deficient Mice," *Cancer Research*, vol 64, pp. 4699-4702, 2004.

* cited by examiner

*Primary Examiner*—Robert Landsman
*Assistant Examiner*—Ian Dang
(74) *Attorney, Agent, or Firm*—Drinker Dibble & Reath, LLP

(57) ABSTRACT

The present invention relates to the inhibition of angiogenesis by neutrophil alpha-defensins. Further, the present invention relates to methods involving the inhibition of endothelial cell adhesion to the extracellular matrix, endothelial cell apoptosis, and endothelial cell angiogenesis.mediated by alpha-defensins.

2 Claims, 7 Drawing Sheets

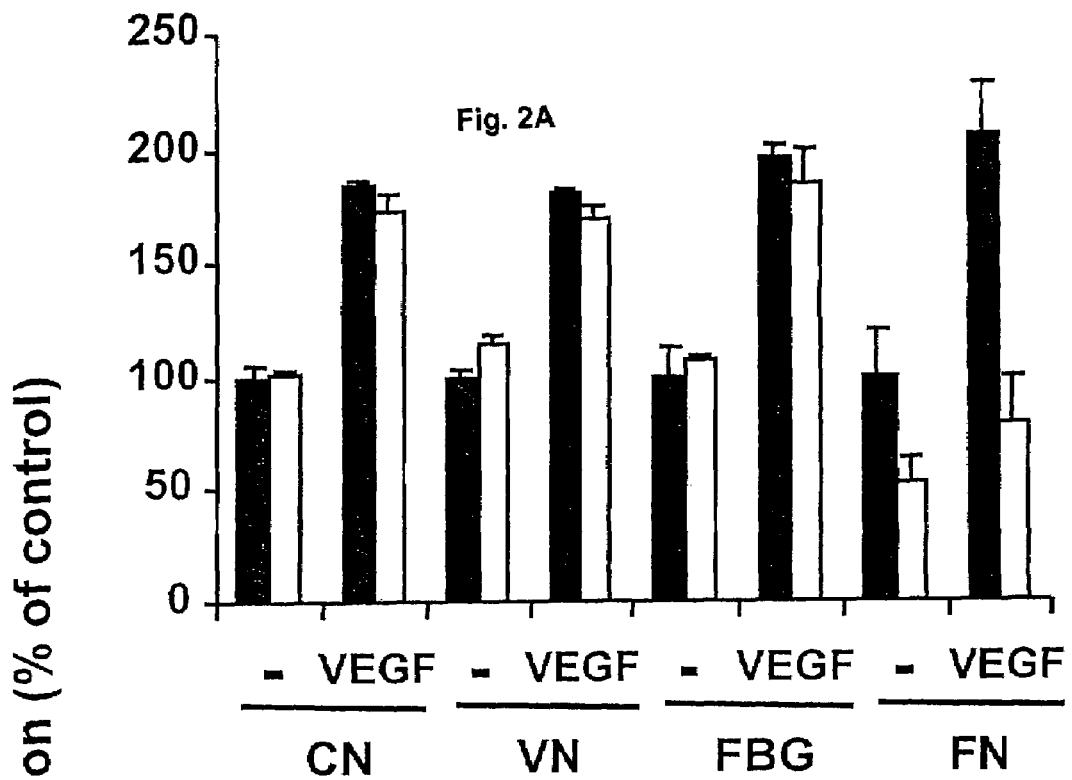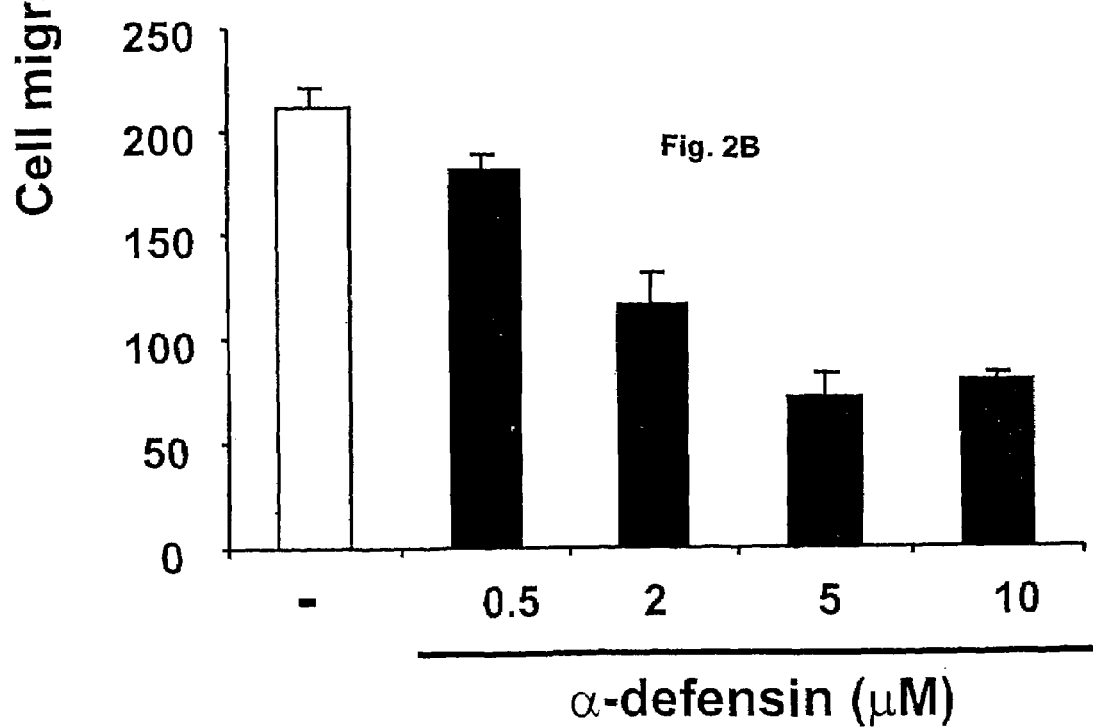

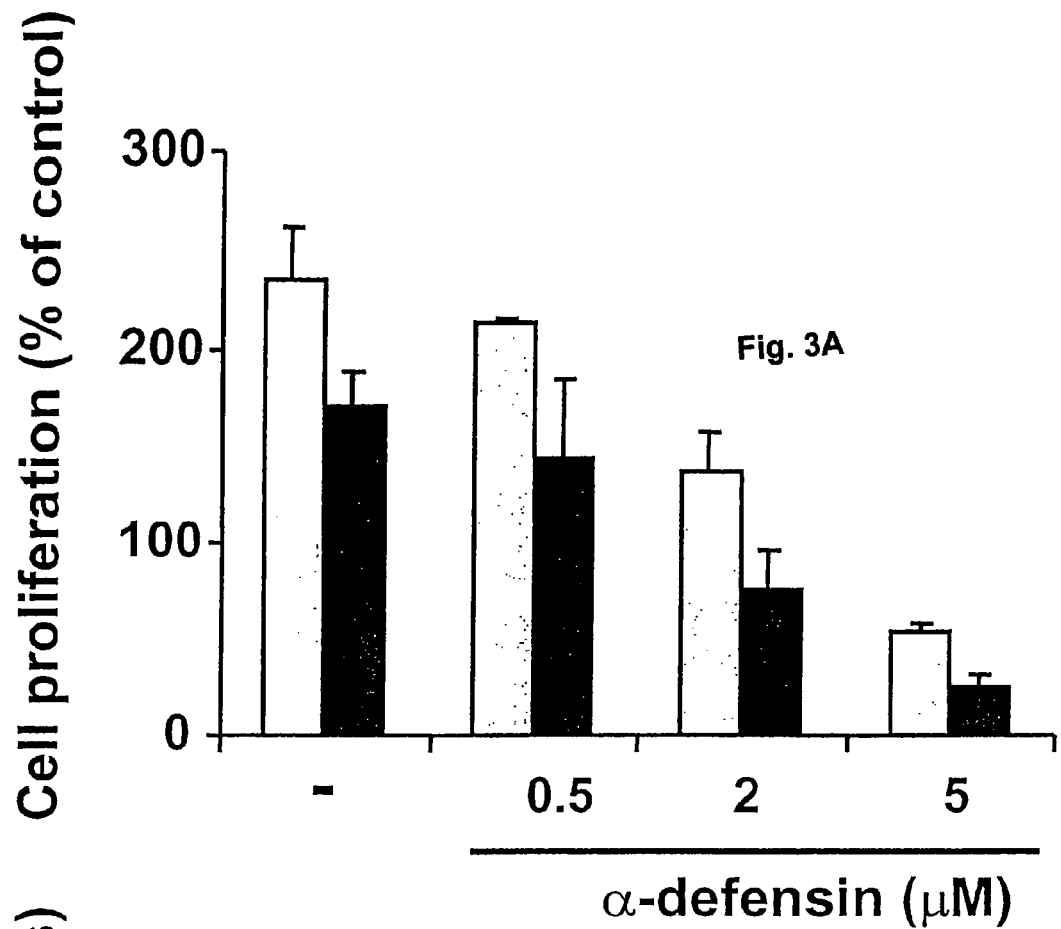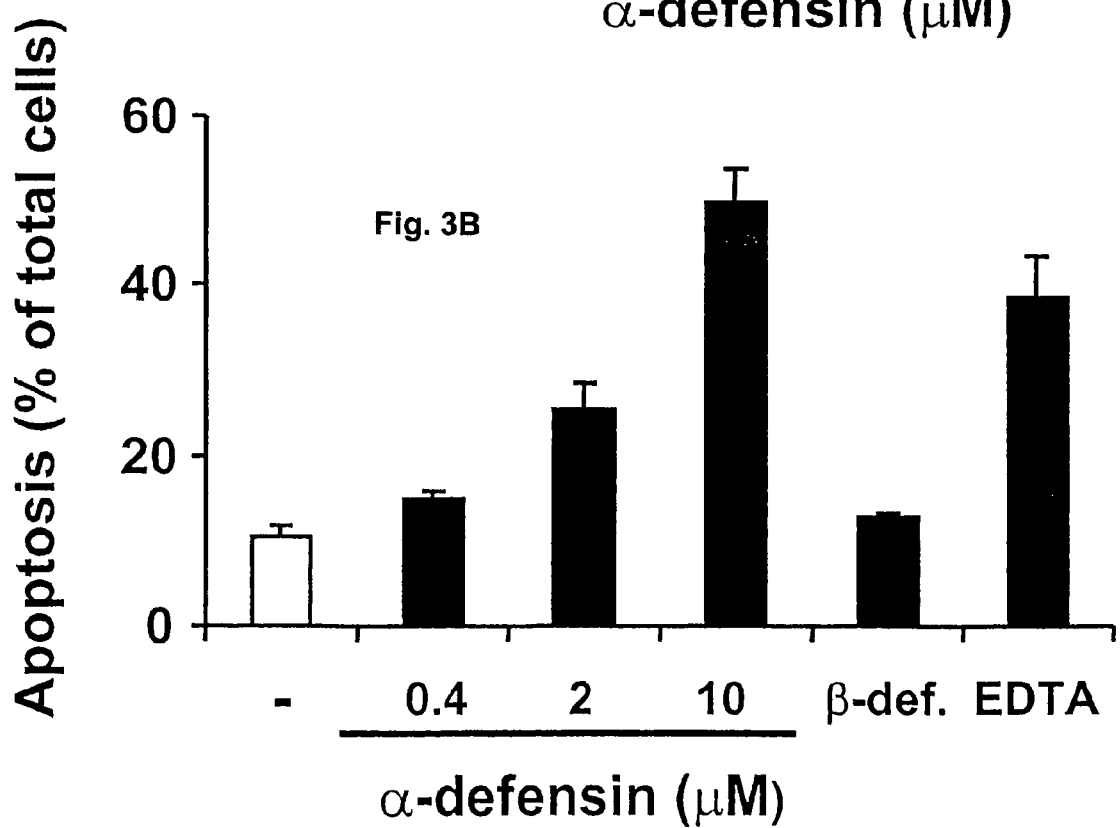

Fig. 4A
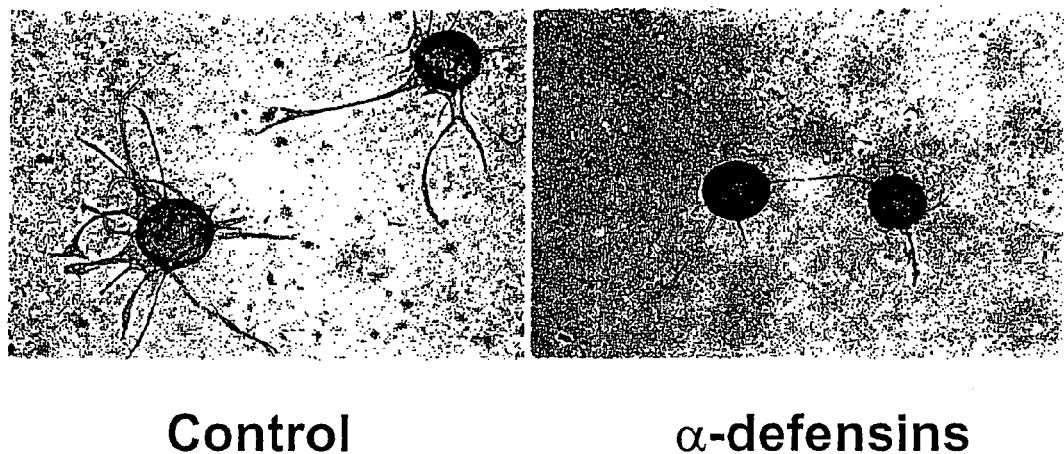
Control        α-defensins
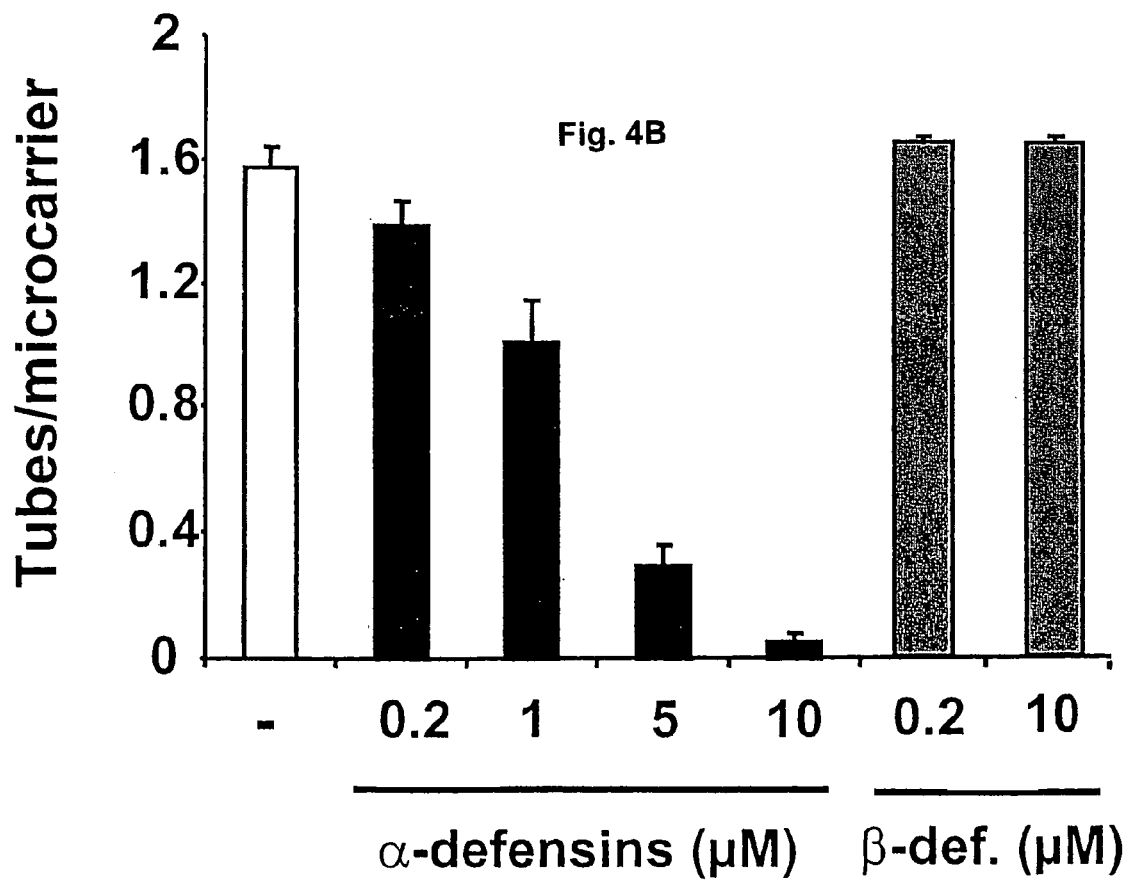

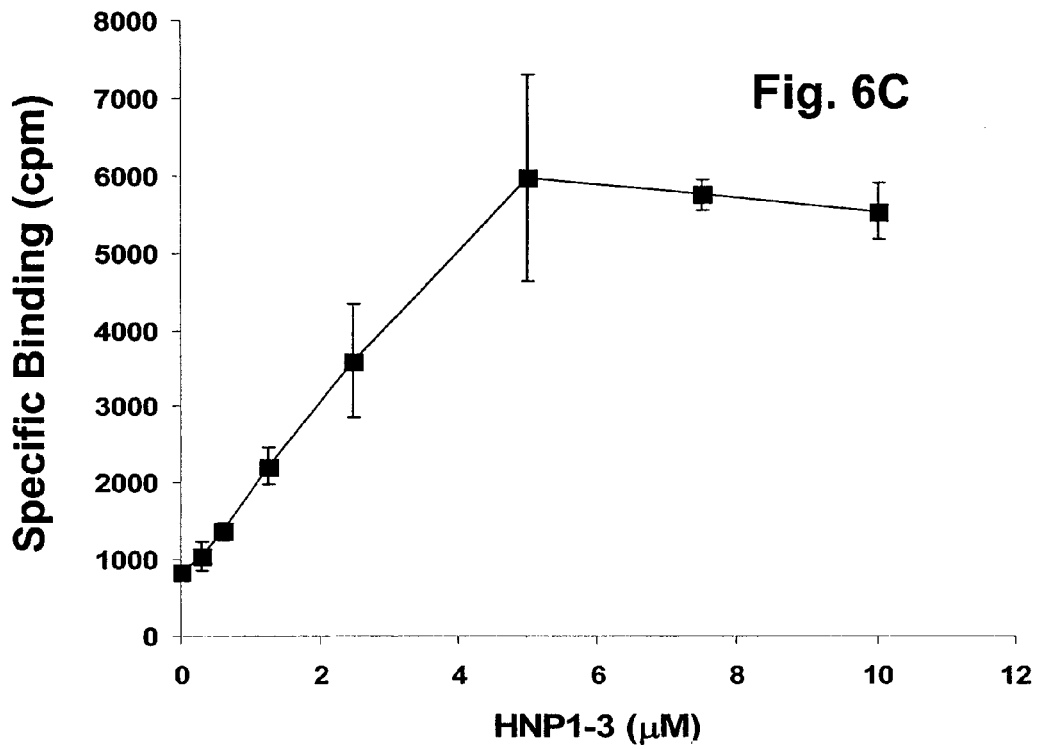
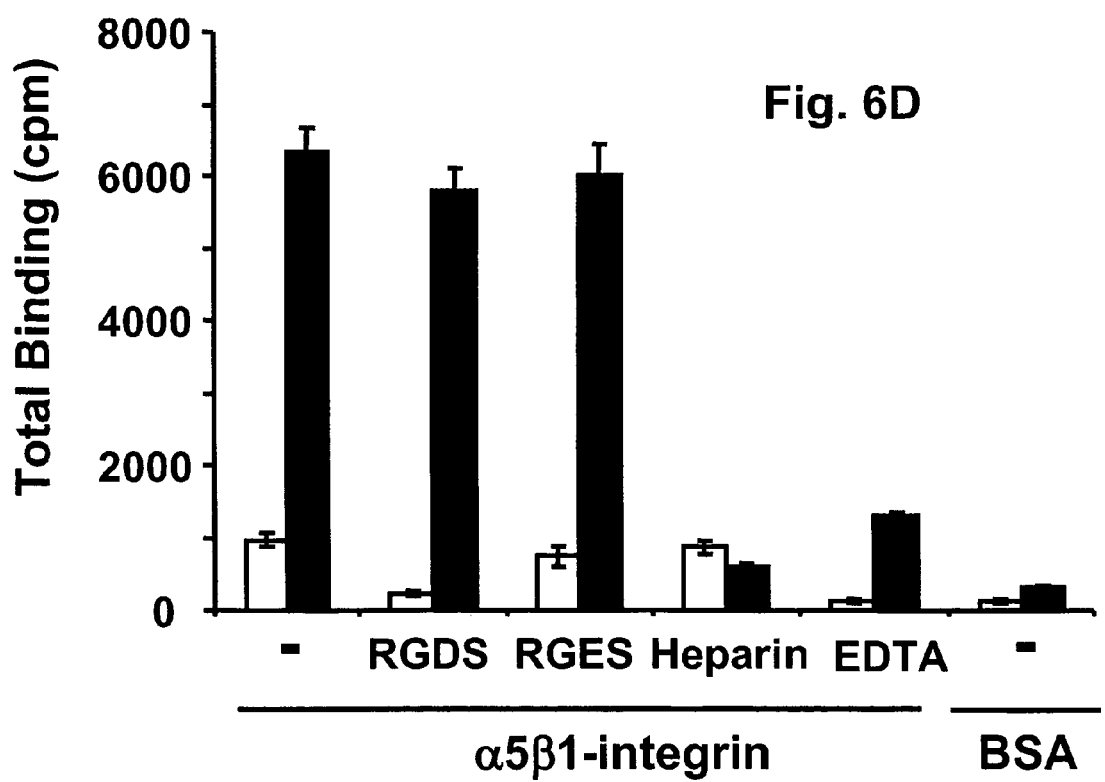

INHIBITION OF ADHESION AND MIGRATION OF AN ENDOTHELIAL CELL TO FIBRONECTIN BY NEUTROPHIL ALPHA-DEFENSINS

CROSS REFERENCE TO RELATED APPLICATIONS

This application is a continuation of U.S. patent application Ser. No. 10/983,527, filed Nov. 8, 2004, now abandoned, which claims the benefit of priority pursuant to 35 U.S.C. 119(c) to U.S. Provisional Patent Application No. 60/518,443, filed on Nov. 7, 2003, all of which are incorporated by reference in their entirety herein.

STATEMENT REGARDING FEDERALLY SUPPORTED RESEARCH OR DEVELOPMENT

This research was supported in part by U.S. Government funds (National Institutes of Health grant HL58107) and the U.S. Government may therefore have certain rights in the invention.

BACKGROUND OF THE INVENTION

Angiogenesis, the development and growth of new blood vessels, is important for organ development, wound healing and various pathological conditions such as tumor growth. Angiogenesis involves several processes, such as changes in vascular permeability, as well as endothelial cell adhesion, migration, proliferation and differentiation (Folkman, J. et al., 1996, *Cell* 87:1153-5). These processes depend both on a number of growth factors as well as on adhesive contacts with the extracellular matrix (ECM) (Breier, G., A. et al., 1997, *Thromb. Haemost.* 8:678-683, Risau, W., 1997, *Nature* 386: 671-674, Strombald, S. et al., 1996, *Chem. Biol.* 3:881-885). ECM-associated proteins, such as fibronectin (FN), vitronectin (VN) and fibrinogen (FBG) are deposited into an adhesive fibrillar network and control cellular function including growth, differentiation and migration by transmitting signals to the cells through specific integrins (Giancotti, F. G. et al., 1999, *Science* 285:1028-32). Observations that mice lacking FN and its receptor α5β1 die early in development and exhibit an improperly formed vasculature indicate that both proteins are crucial participants in physiologic angiogenesis (Fassler, R. et al., 1995, *Genes Dev.* 9:1896-1908, George, E. L. et al., 1993, *Development* 119:1079-1091, Yang, J. T. et al., 1993, *Development* 119:1093-1105). Results of in vitro and in vivo studies provide evidence that FN and αβ1 are critically involved in tumor angiogenesis as well (Hynes, R. O., 2002, *Nat. Med.* 8:918-921, Kim, S. et al., 2000, *Am. J. Pathol.* 156:1345-1362).

There is emerging evidence that inflammatory cells, and particularly neutrophils, regulate endothelial cell functions related to angiogenesis. Both pro-angiogenic and anti-angiogenic activities of neutrophils have been described. Neutrophils are a source of growth factors such as the vascular endothelial growth factor (VEGF) and matrix metalloproteinases (Shamamian, P. et al., 2001, *J. Cell. Physiol.* 189:197-206, Lee, S. et al., 2002, *J. Clin. Invest.* 110:1105-11; Webb, N. J. et al., 1998, *Cytokine.* 10:254-7). On the other hand, neutrophil-derived elastase can generate the anti-angiogenic factor angiostatin (Scapini, P. et al., 2002, *J. Immunol.* 168: 5798-804). The net effect of these and potentially other angiogenic products of neutrophils may depend on the biological context, but the manner in which neutrophils regulate angiogenesis in vivo has not been rigorously investigated.

α-defensins, a family of four closely related anti-microbial peptides, are the most abundant proteins found in neutrophil granules, comprising approximately 5% of the total neutrophil protein content (Ganz, T. 2002., *J. Clin. Invest.* 109:693-697). α-defensins are secreted when neutrophils are activated during phagocytosis of microorganisms or by specific exogenous inflammatory agonists. As small cationic peptides, α-defensins can be incorporated into the cell membrane of prokaryotic organisms during phagocytosis, disrupting ion fluxes and provoking cell lysis (Ganz, T. 2002, *J. Clin. Invest.* 109:693-697, Kagan, B. L. et al., 1994, *Toxicology* 87:131-149, Ganz, T. et al., 1985, *J. Clin. Invest.* 76:1427-35, Harwig, S. S. et al., 1994, *Methods Enzymol.* 236:160-172). During severe infections, α-defensins are released into the plasma at concentrations approaching 30 μM (whereas such concentrations are normally 15 nM) (Panyutich, A. V. et al., 1993, *J. Lab. Clin. Med.* 122:202-207). α-defensins accumulate in the vessel wall by binding to ECM-associated FN (Bdeir, K. et al., 1999, *Blood* 94:2007-2019) and are abundant in human atherosclerotic plaques (Bdeir, K. et al., 1999, *Blood* 94:2007-2019, Barnathan, E. S. et al., *Am. J. Pathol.* 150: 1009-20); they promote the accumulation of lipoprotein(a) (Higazi, A. A. et al., 1997, *Blood* 8 9:4290-4298) and inhibit plasminogen activation (Higazi, A. A. et al, 1996, *J. Biol. Chem.* 271: 17650-17655).

The role of α-defensins in neutrophil biology has heretofore been poorly understood, for example, with respect to neutrophil biology related to tumors. While it is known that tumor vascularization is essential to the growth of tumors in a variety of pathophysiological conditions, it is not known whether α-defensins play any role in neutrophil activity related to tumor biology.

Proliferative retinopathies are major causes of blindness. The prominent feature of these retinopathies is the exuberant neovascularization, which is orchestrated by the hypoxia-induced upregulation of vascular endothelial growth factor (VEGF) that stimulates endothelial cell proliferation, permeability and migration/invasion, as well as by the interaction of extracellular matrix components like fibronectin (FN) with their integrin receptors.

Pathological neovascularization, for example, is a major cause of blindness in infancy and during adulthood, complicating such disorders as the retinopathy of prematurity, sickle cell anemia and diabetes, among others. Neutrophil activation is part of each of these processes, but has been heretofore unknown if α-defensin naturally participates in controlling these processes, or if α-defensin may have any role in the control of these devastating complications.

Because the management and/or inhibition of tumor vascularization is an attractive target for controlling or preventing tumor growth, an understanding of the role of neutrophils, and thereby, α-defensins, in tumor vascularization and related biology is critical to the development of novel anti-angiogenesis therapeutics useful in the treatment of cancer, as well as other diseases, such as retinopathies associated with exuberant and pathological vascular growth. The present invention provides the understanding and goes further to develop therapies and therefore meets these needs.

SUMMARY OF THE INVENTION

In one embodiment, the present invention features a method of inhibiting adhesion of an endothelial cell to an extracellular matrix (ECM), the method comprising contacting an endothelial cell with an isolated α-defensin in an amount sufficient to inhibit adhesion to an ECM. In one aspect, the method is conducted in vivo. In another aspect, the method is conducted in vitro.

In one embodiment, a method of the invention includes an α-defensin which inhibits the adhesion of said endothelial cell to fibronectin. In another embodiment, α-defensin inhibits the migration of an endothelial cell to fibronectin.

In one embodiment, the present invention features a method of inhibiting migration of an endothelial cell to an ECM, the method comprising contacting an endothelial cell with an isolated α-defensin in an amount sufficient to inhibit migration to an ECM.

In an embodiment of the invention, a method of inhibiting adhesion of an endothelial cell to fibronectin comprises contacting an endothelial cell with an isolated α-defensin in an amount sufficient to inhibit adhesion to fibronectin. In one embodiment, the method is conducted in vivo. In another embodiment, the method is conducted in vitro.

In one embodiment of the invention, a method of inhibiting migration of an endothelial cell to fibronectin comprises contacting an endothelial cell with an isolated α-defensin in an amount sufficient to inhibit migration to fibronectin. In another embodiment of the invention, a method of inhibiting adhesion of an endothelial cell to fibronectin comprises contacting fibronectin with an isolated α-defensin in an amount sufficient to inhibit endothelial cell adhesion to fibronectin. In yet another embodiment of the invention, a method of inhibiting migration of an endothelial cell to fibronectin comprises contacting fibronectin with an isolated α-defensin in an amount sufficient to inhibit migration of an endothelial cell to fibronectin.

In one embodiment, the present invention features a method of inhibiting endothelial cell proliferation, the method comprising contacting an endothelial cell with an isolated α-defensin in an amount sufficient to inhibit endothelial cell proliferation. In another embodiment, the invention features a method of inducing apoptosis in an endothelial cell, the method comprising contacting an endothelial cell with an isolated α-defensin in an amount sufficient to induce apoptosis in said cell.

In an embodiment, the invention also features a method of inhibiting angiogenesis in an in vitro system, the method comprising contacting an endothelial cell with an isolated α-defensin in an amount sufficient to inhibit angiogenesis. In another embodiment, the invention features a method of inhibiting angiogenesis in vivo comprising contacting endothelial cell with an isolated α-defensin in an amount sufficient to inhibit angiogenesis.

In an embodiment of the invention, a method of inhibiting capillary-like tube formation in an in vitro system comprises contacting an endothelial cell with an isolated α-defensin in an amount sufficient to inhibit capillary-like tube formation. In another embodiment of the invention, a method of inhibiting capillary formation in vivo comprises contacting an endothelial cell with an isolated α-defensin in an amount sufficient to inhibit capillary formation. In yet another embodiment, the invention features a method of inhibiting neovascularization comprising contacting endothelial cell with an isolated α-defensin in an amount sufficient to inhibit angiogenesis.

In an embodiment, the invention features a method of modulating a biological condition associated with an endothelial cell in a mammal, the method comprising administering an isolated α-defensin to a mammal in an amount sufficient to modulate a biological condition. Biological conditions that can be modulated by a method of the invention include, but are not limited to, vasculogenesis, angiogenesis, vasoregulation, thrombosis homeostasis, diabetic retinopathy, macular degeneration, arthritis, asthma, lung injury, atherosclerosis, and solid tumor cancer.

In another embodiment, the invention features a method of identifying a compound that stimulates angiogenesis in a mammal, the method comprising contacting a mammal with a test compound, wherein a higher level of angiogenesis in the mammal contacted with the test compound compared with the level of angiogenesis in a second otherwise identical mammal not contacted with the test compound is an indication that the test compound increases the level of angiogenesis in the mammal. In one aspect, the test compound inhibits the interaction between α-defensin and an endothelial cell.

In an embodiment, the invention features a method of identifying a compound that inhibits angiogenesis in a mammal comprising contacting a mammal with a test compound, wherein a lower level of angiogenesis in a mammal contacted with the test compound compared with the level of angiogenesis in a second otherwise identical mammal not contacted with the test compound is an indication that the test compound decreases the level of angiogenesis in the mammal. In one aspect, the test compound enhances the interaction between α-defensin and an endothelial cell.

In an embodiment, the invention also features a method of treating a disease mediated by hyper-proliferation of endothelial cells in a mammal, the method comprising administering to a mammal afflicted with a disease mediated by hyper-proliferation of endothelial cells an endothelial cell-inhibiting amount of an α-defensin.

In one embodiment, the invention further features a kit for modulating a biological process associated with an endothelial cell. Such a kit includes at least one α-defensin, an applicator, and instructional material, wherein the instructional material includes instructions for the use of the kit to modulate a biological process associated with an endothelial cell, and instructions for the use of an α-defensin for the purpose of modulating a biological process associated with an endothelial cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2A is a graph depicting the effect of α-defensin on endothelial cell migration. Migration of HUVEC towards collagen (CN), vitronectin (YN), fibrinogen (FBG) and fibronectin (FN) is shown alone or after the addition of VEGF and in the absence (filled bars) or presence of α-defensin (open bars) (5 μM).

FIG. 2B is a graph depicting the effect of α-defensin on endothelial cell migration. VEGF-stimulated migration of HUVEC towards FN is shown in the absence (−; open bar) or presence (filled bars) of increasing concentrations of α-defensin, as indicated. Cell migration is expressed as % of control, which is represented as cell migration in the absence of any stimulus or competitor. Data are Mean+/−STD (n=3) of a typical experiment; similar results were obtained in three separate experiments.

FIG. 3A is a graph depicting the effect of α-defensin on endothelial cell proliferation and apoptosis. Proliferation of HUVEC was examined by measuring the incorporation of bromodeoxyuridine (BRDU). HUVEC were incubated with 10 ng/ml VEGF (open bars) or 1 μM sphingosine-1-phosphate (SPP, filled bars) in the absence (−) or presence of increasing concentrations of α-defensin as indicated. Proliferation of HUVEC is expressed as % of control, defined as cell proliferation in the absence of any stimulus or competitor.

FIG. 3B is a graph depicting the effect of α-defensin on endothelial cell proliferation and apoptosis. The apoptosis of HUVEC is shown in the absence (−; open bar) or presence (filled bars) of increasing concentrations of α-defensin, of β-defensin (10 μM) or EDTA (5 mM) as indicated. The number of apoptotic cells is expressed as % of the total cell number. Data are Mean+/−STD (n=3) of a typical experiment; similar results were obtained in three separate experiments.

FIG. 4A is a collection of images depicting the effect of α-defensin on in vitro capillary-like tube formation. Images of formed tubes in the presence of 0.1% ECGS and in the absence ("control;" left panel) or presence of 5 μM α-defensins ("α-defensins;" right panel) are shown.

FIG. 4B is a graph depicting the effect of α-defensin on in vitro capillary-like tube formation. Capillary-like tube formation was performed with bovine retinal endothelial cells (BREC). BREC were incubated for 48 h with 0.1% ECGS in the absence (−; open bar) or presence of increasing concentrations of α-defensin (filled bars) or β-defensin (gray bars), as indicated. Capillary-like tube formation is expressed as tubes/microcarrier bead. Data are Mean+/−STD (n=3) of a typical experiment; similar results were obtained in three separate experiments.

FIG. 6C is a graph depicting the effect of α-defensin on the binding of FN to α5β1-integrin. Binding of $^{125}$I-FN (1 nM) to immobilized α5β1-integrin (2.5 μg/ml) is shown in the absence or presence of increasing concentrations of HNPs as described in panel A. Specific binding was defined as the difference between binding in the presence of 2 mM $MnCl_2$ and the binding in the presence of 10 mM EDTA which served as non-specific binding control.

FIG. 6D is a graph depicting the effect of α-defensin Binding of $^{125}$I-FN (1 nM) to immobilized α5β1-integrin (2.5 μg/ml) or to immobilized BSA is shown in the absence (open bars) or presence of HNPs (filled bars, 5 μM) without (−) or with RGDS or RGES (1 mg/ml), heparin (4 units/ml), or EDTA (10 mM). Total binding is shown. Data are shown as the Mean±STD (n=3) of three separate experiments.

DETAILED DESCRIPTION OF THE INVENTION

Figure 1A:
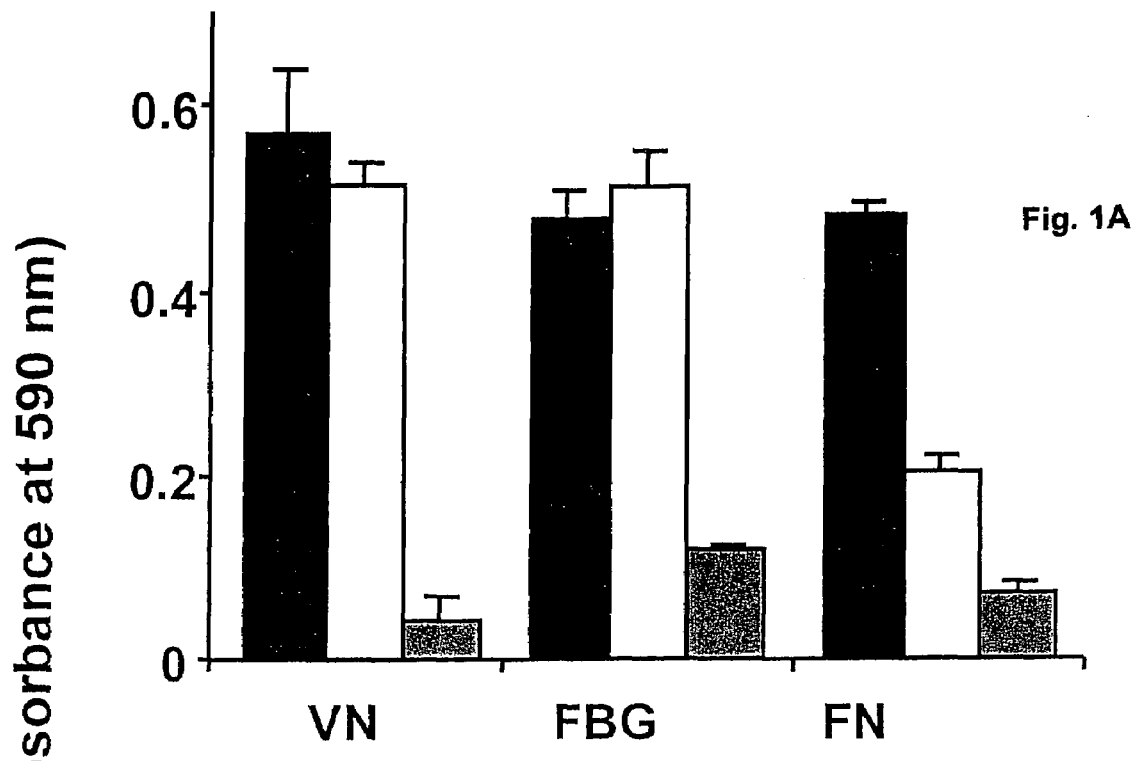
FIG. 1A is a graph depicting the effect of α-defensin on endothelial cell adhesion. Adhesion of human umbilical vein endothelial cells (HUVEC) to immobilized vitronectin (VN), fibrinogen (FBG) and fibronectin (FN) (each at 5 pg/ml) is shown in the absence (filled bars) or presence of α-defensin (open bars, 5 μM), or a blocking antibody against αvβ3-integrin (for VN and FBG) or against 131-integrin (gray bars, antibody concentration 20 μg/ml).

Angiogenesis, the growth of new blood vessels, is a complex biological process that is orchestrated by several growth factors and components of the extracellular matrix, including fibronectin (FN) and its receptor, the integrin α5β1. Angiogenesis is a critical part of inflammation and wound repair, but the mechanism by which vascular proliferation and migration is regulated by inflammatory cells has heretofore been incompletely understood. As disclosed herein for the first time, α-defensins act as a link between inflammation and angiogenesis. The present invention is based, in part, on the discovery that α5β1-mediated endothelial cell adhesion and migration to FN is inhibited specifically and in a dose-dependent manner by α-defensins. The data disclosed herein also demonstrate, for the first time, that α-defensins inhibit capillary tube formation in three-dimensional fibrin-matrices. Further, the present invention is based, in part, on the discovery that α-defensins inhibit neovascularization in vivo.

Therefore, in one aspect, the present invention features compositions and methods comprising α-defensins useful for regulating angiogenesis by affecting endothelial cell adhesion. The present invention also features, in another aspect, compositions and methods useful for regulating angiogenesis by affecting endothelial cell migration in a FN-dependent manner. The present invention also features compositions and methods comprising α-defensins useful for regulating endothelial cell proliferation. Therefore, the present invention provides insight into the role of inflammatory cells in angiogenesis and provides a platform for developing a novel anti-angiogenesis drugs, among other applications.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" a disease, disorder or condition means reducing the severity of one or more symptoms of the disease, disorder or condition.

By the term "applicator" as the term is used herein, is meant any device including, but not limited to, a hypodermic syringe, a pipette, a bronchoscope, a nebulizer, and the like, for administering the CTHRC1 nucleic acid, protein, and/or composition of the invention to a mammal.

As used herein, an "instructional material" includes a publication, a recording, a diagram, or any other medium of expression which can be used to communicate the usefulness of the nucleic acid, peptide, and/or composition of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

By the term "specifically binds," as used herein, is meant a compound, e.g., a protein, a nucleic acid, an antibody, and the like, which recognizes and binds a specific molecule, but does not substantially recognize or bind other molecules in a sample.

As used herein, to "treat" means reducing the frequency with which symptoms of a disease, disorder, or adverse condition, and the like, are experienced by a patient.

As the term is used herein, "modulation" of a biological process refers to the alteration of the normal course of the biological process. For example, modulation of angiogenesis may involve inhibition of the angiogenic process. Alternatively, modulation of angiogenesis may involve stimulation of the angiogenic process. Similarly, "modulation" of any process or interaction is also encompassed by the present invention. For example, modulation of the interaction of an endothelial cell with fibronectin may involve inhibition of the interaction of an endothelial cell with fibronectin or it may involve promotion or enhancement of an endothelial cell with fibronectin.

As used herein, the term "extracellular matrix" or "ECM" refers to material surrounding and supporting cells located within mammalian tissues. The ECM may also be referred to as connective tissue, and is comprised of three major classes of biomolecules, including structural proteins (e.g., collagen and elastin), specialized proteins (e.g. fibrillin, fibronectin, laminin), and proteoglycans.

The term "α-defensin" refers to any one of human neutrophil peptides 1, 2, 3, or 4, and human defensins 5 or 6, also known as HNP-1, HNP-2, HNP-3, HNP-4 HD5, and HD6 respectively.

DESCRIPTION OF THE INVENTION

Methods

A. Methods of Modulating Endothelial Cell Properties and Functions

In one aspect, the present invention features a method of inhibiting a biological interaction of an endothelial cell. In one embodiment, the present invention features a method of inhibiting the interaction of an endothelial cell with an extracellular matrix (ECM). As described in detail elsewhere herein, α-defensin is useful to inhibit the adhesion of an endothelial cell to an ECM. This is because it has been shown herein for the first time that α-defensin inhibits that adhesion of an endothelial cell to an ECM.

Therefore, one embodiment of the present invention features a method of inhibiting endothelial cell adhesion to an ECM by contacting an endothelial cell with α-defensin, wherein the α-defensin inhibits adhesion of an endothelial cell to an ECM. In another embodiment, a method of the invention features a method of inhibiting endothelial cell adhesion to an ECM by contacting the ECM with α-defensin, wherein the α-defensin inhibits adhesion of the endothelial cell to the ECM. In yet another embodiment of the invention, adhesion of an endothelial cell to an ECM is inhibited by contacting both the endothelial cell and the ECM with α-defensin.

As will be understood by the skilled artisan based on the disclosure set forth herein, α-defensin useful in the present invention may be a homogeneous preparation, or it may be a heterogeneous preparation. That is, a single species of α-defensin may be used in a method of the present invention. Alternatively, a mixture of two or more different α-defensins may be used in a method of the present invention. The preparation, identification and use of α-defensins of the present invention is set forth in detail elsewhere herein.

The present invention also features a method of inhibiting the interaction of an endothelial cell with fibronectin. This is because it has been shown herein for the first time that α-defensin inhibits adhesion of an endothelial cell to fibronectin. In one aspect, a method of the invention useful for inhibiting the interaction of an endothelial cell with fibronectin comprises contacting an endothelial cell with α-defensin, wherein the α-defensin inhibits adhesion of the endothelial cell to fibronectin. In another embodiment, a method of the invention useful for inhibiting the interaction of an endothelial cell with fibronectin comprises contacting fibronectin with α-defensin, wherein the α-defensin inhibits adhesion of the endothelial cell to fibronectin. In yet another embodiment of the invention, adhesion of an endothelial cell to fibronectin is inhibited by contacting both the endothelial cell and fibronectin with α-defensin.

In one aspect, the present invention features a method of inhibiting a biological migration of an endothelial cell. In one embodiment, the present invention features a method of inhibiting the migration of an endothelial cell to an extracellular matrix (ECM). As described in detail elsewhere herein, α-defensin is useful to inhibit the migration of an endothelial cell to an ECM. This is because it has been shown herein for the first time that α-defensin inhibits the migration of an endothelial cell to an ECM.

Therefore, one embodiment of the present invention features a method of inhibiting endothelial cell migration to an ECM by contacting an endothelial cell with α-defensin, wherein the α-defensin inhibits migration of an endothelial cell to an ECM. In another embodiment, a method of the invention features a method of inhibiting endothelial cell migration to an ECM by contacting the ECM with α-defensin, wherein the α-defensin inhibits migration of the endothelial cell to the ECM. In yet another embodiment of the invention, migration of an endothelial cell to an ECM is inhibited by contacting both the endothelial cell and the ECM with α-defensin.

The present invention also features a method of inhibiting the biological migration of an endothelial cell to fibronectin. This is because it has been shown herein for the first time that α-defensin inhibits migration of an endothelial cell to fibronectin. In one aspect, a method of the invention useful for inhibiting the migration of an endothelial cell to fibronectin comprises contacting an endothelial cell with α-defensin, wherein the α-defensin inhibits migration of the endothelial cell to fibronectin. In another embodiment, a method of the invention useful for inhibiting the migration of an endothelial cell to fibronectin comprises contacting fibronectin with α-defensin, wherein the α-defensin inhibits migration of the endothelial cell to fibronectin. In yet another embodiment of the invention, migration of an endothelial cell to fibronectin is inhibited by contacting both the endothelial cell and fibronectin with α-defensin.

In one aspect, the present invention features a method of inducing or stimulating a biological process of an endothelial cell. In one embodiment, the present invention features a method of inducing apoptosis of an endothelial cell. As described in detail elsewhere herein, α-defensin is useful to induce apoptosis of an endothelial cell. This is because it has been shown herein for the first time that α-defensin induces apoptosis in an endothelial cell.

Therefore, one embodiment of the present invention features a method of inducing endothelial cell apoptosis by contacting an endothelial cell with α-defensin, wherein the α-defensin induces apoptosis of the endothelial cell. In another embodiment, the invention features a method of inducing apoptosis of an endothelial cell by contacting an ECM with α-defensin, wherein interaction between the endothelial cell and the ECM provides α-defensin to the endothelial cell, and the α-defensin thereby induces apoptosis of the endothelial cell. In yet another embodiment of the invention, apoptosis of an endothelial cell is induced by contacting both the endothelial cell and the ECM with α-defensin.

In another embodiment of the present invention is provided a method of inducing apoptosis of an endothelial cell by contacting fibronectin with α-defensin, wherein interaction between the endothelial cell and fibronectin provides α-defensin to the endothelial cell, and the α-defensin thereby induces apoptosis of the endothelial cell. In yet another embodiment of the invention, apoptosis of an endothelial cell is induced by contacting both the endothelial cell and fibronectin with α-defensin.

In another aspect, the present invention features a method of inhibiting a biological process of an endothelial cell. In one embodiment, the present invention features a method of inhibiting the proliferation of an endothelial cell. As described in detail elsewhere herein, α-defensin is useful to inhibit the proliferation of an endothelial cell. This is because it has been shown herein for the first time that α-defensin inhibits proliferation of an endothelial cell.

Therefore, one embodiment of the present invention features a method of inhibiting endothelial cell proliferation by contacting an endothelial cell with an α-defensin, wherein the α-defensin inhibits proliferation of the endothelial cell. In another embodiment, the invention features a method of inhibiting proliferation of an endothelial cell by contacting an ECM with α-defensin, wherein interaction between the endothelial cell and the ECM provides α-defensin to the endothelial cell, and the α-defensin thereby inhibits proliferation of the endothelial cell. In yet another embodiment of the invention, proliferation of an endothelial cell is inhibited by contacting both the endothelial cell and the ECM with α-defensin.

In another embodiment of the present invention is provided a method of inhibiting proliferation of an endothelial cell by contacting fibronectin with α-defensin, wherein interaction between the endothelial cell and fibronectin provides α-defensin to the endothelial cell, and the α-defensin thereby inhibits proliferation of the endothelial cell. In yet another embodiment of the invention, inhibition of the proliferation of an endothelial cell is induced by contacting both the endothelial cell and fibronectin with α-defensin.

The present invention also features a method of modulating processes and functions associated with endothelial cells. As described in detail elsewhere herein, in vitro and in vivo processes and functions associated with endothelial cells can be modulated by α-defensin. In one aspect of the invention, a method of inhibiting an endothelial cell process or function in vitro is provided.

In one embodiment, a method of inhibiting an endothelial cell process or function in vitro includes contacting an endothelial cell with α-defensin, whereby the α-defensin inhibits a process or a function associated with the endothelial cell. In one aspect, a method of the invention is useful for inhibition of angiogenesis in vitro. In another aspect, a method of the invention is useful for inhibition of capillary-like tube formation in vitro.

Another aspect of the invention provides a method for inhibiting migration of an endothelial cell to an ECM. In still another aspect, a method of the invention is useful for inhibition of migration of an endothelial cell to fibronectin. In another aspect of the invention, a method is provided for inhibition of the adhesion of an endothelial cell to an ECM. In still another aspect, a method is provided for the inhibition of an endothelial cell to fibronectin.

The present invention also features a method of inhibiting processes and functions associated with endothelial cells in vivo. In one aspect of the invention, a method of inhibiting a process or function of an endothelial cell in vivo includes contacting an endothelial cell with α-defensin, whereby the α-defensin inhibits a process or a function associated with the endothelial cell in vivo. In one embodiment, a method of the invention inhibits angiogenesis in vivo. In another embodiment, a method of the invention inhibits capillary-like tube formation in vivo. In yet another embodiment, a method of the invention inhibits neovascularization in vivo.

The present invention also features a method of inhibiting an endothelial cell-associated biological process in a living organism. As described in detail elsewhere herein, α-defensins have been shown by way of the present invention to possess anti-angiogenic activity in chicken. That is, data presented herein demonstrate that angiogenesis is inhibited in a living organism upon contacting the organism with α-defensin. As described herein, such inhibition occurs at or near the location of contact with α-defensin.

As set forth elsewhere herein for the first time, the ability of α-defensin to inhibit endothelial cell migration to ECM and fibronectin, the ability of α-defensin to inhibit endothelial cell adhesion to ECM and fibronectin, and the ability of α-defensin to inhibit endothelial cell proliferation and to induce endothelial cell apoptosis all confer anti-angiogenic or anti-vascularization properties upon α-defensin. In particular, the properties of α-defensin disclosed herein for the first time demonstrate the roles of α-defensin in biological processes related to inflammation, wound healing, vascularization, angiogenesis, diabetic retinopathy, macular degeneration, arthritis, asthma, lung injury, atherosclerosis, exuberant angiogenesis leading to blindness, and solid tumors, among others.

Therefore, the present invention includes methods of modulating a biological process using α-defensin. Based on the disclosure provided herein for the first time, one of skill in the art will understand that any biological process in which α-defensin plays a role is a biological process that may be modulated by α-defensin according to the present invention.

One example of the modulation of a biological process according to the present invention includes the treatment of a patient that may benefit from modulation of an endothelial cell-related biological process by way of an α-defensin-based method or composition, which compositions are addressed elsewhere herein. By way of a non-limiting example, a method of the present invention is useful to treat a patient that can benefit from inhibition of angiogenesis. As set forth in detail elsewhere herein, it has been found that α-defensin can be used to inhibit angiogenic properties of an endothelial cell, including, but not limited to endothelial cell migration to an ECM, endothelial cell migration to fibronectin, and endothelial cell proliferation. Therefore, in one embodiment, the present invention provides a method of inhibiting angiogenesis in a patient in need thereof by contacting an endothelial cell of the patient with at least one α-defensin.

It will be understood by the skilled artisan, when equipped with the present disclosure, that methods set forth herein that are useful in vivo are equally applicable to the treatment of a patient that may benefit from such treatment.

In another aspect of the present invention, a method of inhibiting a biological process using α-defensin is provided. In one embodiment, the invention features a method of inhibiting vasculogenesis. A method of inhibiting vasculogenesis according to the present invention includes contacting an endothelial cell with α-defensin, whereby vasculogenesis is inhibited. The present invention also features a method of inhibiting neovascularization. In one embodiment, a method of inhibiting neovascularization includes contacting an endothelial cell with α-defensin, whereby neovascularization is inhibited.

In another embodiment, the invention features a method of inhibiting angiogenesis. A method of inhibiting angiogenesis according to the present invention includes contacting an endothelial cell with α-defensin, whereby angiogenesis is inhibited. In one aspect, a method of inhibiting angiogenesis includes inhibiting exuberant angiogenesis that leads to blindness. Further still, the present invention also features a method of inhibiting angiogenesis at a site of inflammation. In one embodiment, a method of inhibiting angiogenesis at a site of inflammation includes contacting an endothelial cell with α-defensin, thereby inhibiting angiogenesis at a site of inflammation.

As described elsewhere herein, contacting an ECM or fibronectin with α-defensin is also useful in methods of the present invention. By way of a non-limiting example, a method including contacting an ECM or fibronectin with an α-defensin may be used to inhibit angiogenesis, wherein the ECM or fibronectin provides α-defensin to an endothelial cell, thereby inhibiting angiogenesis.

Therefore, the present invention also features a method of modulating a biological process using α-defensin, wherein the method includes contacting an ECM or fibronectin with α-defensin. Based on the disclosure provided herein for the first time, one of skill in the art will understand that any biological process in which α-defensin plays a role is a biological process that may be modulated by contacting an ECM or fibronectin α-defensin according to the present invention.

In one aspect of the present invention is provided a method of inhibiting a biological process by contacting an ECM or fibronectin with α-defensin. In one embodiment, the invention features a method of inhibiting vasculogenesis. A method of inhibiting vasculogenesis according to the present invention includes contacting an ECM or fibronectin with α-defensin, whereby the ECM or fibronectin provides α-defensin to an endothelial cell, thereby inhibiting vasculogenesis. The present invention also features a method of inhibiting neovascularization. In one embodiment, a method of inhibiting neovascularization according to the present invention includes contacting an ECM or fibronectin with α-defensin, whereby the ECM or fibronectin provides α-defensin to an endothelial cell, thereby inhibiting neovascularization.

In another embodiment, the invention features a method of inhibiting angiogenesis. A method of inhibiting angiogenesis according to the present invention includes contacting an ECM or fibronectin with α-defensin, whereby the ECM or fibronectin provides α-defensin to an endothelial cell, thereby inhibiting angiogenesis. Further still, the present invention also features a method of inhibiting angiogenesis at a site of inflammation. In one embodiment, a method of inhibiting angiogenesis at a site of inflammation according to the present invention includes contacting an ECM or fibronectin with α-defensin, whereby the ECM or fibronectin provides α-defensin to an endothelial cell, thereby inhibiting angiogenesis at a site of inflammation.

The present invention also features methods of using α-defensin to modulate other biological processes associated with an endothelial cell. Such processes include, but are not limited to, vasoregulation, and thrombosis homeostasis, as described in detail elsewhere herein.

In one aspect of the invention, modulation of a biological process occurs in vitro. In another aspect, modulation of a biological process occurs in vivo. The present invention also features compositions and methods useful for the treatment of a living organism. In one embodiment, the living organism is a chicken. In another embodiment, the living organism is a mammal, including, but not limited to a human.

One skilled in the art would understand, based upon the disclosure provided herein, that since inhibiting endothelial cell migration and/or adhesion to an ECM, and in particular, to fibronectin, can mediate a beneficial effect, methods of inhibiting migration and/or adhesion of an endothelial cell to an ECM or to fibronectin can be used to treat and/or alleviate a biological process, disease, disorder or condition associated with an endothelial cell in an organism, where a higher level of biological function of an endothelial cell prior to, or in the absence of, treatment provides a benefit. A benefit such as preventing undesired angiogenesis or vascularization is disclosed elsewhere herein.

Thus, whether an α-defensin is administered by contacting an endothelial cell, an ECM, or fibronectin, the present invention includes a method where a biological function of an endothelial cell is modulated in order to treat/or alleviate a disorder associated with endothelial cell biology. Such treatment may include, but is not limited to, inhibition of angiogenesis, inhibition of neovascularization, inhibition of vasculogenesis, and the like. The skilled artisan will know, based on the disclosure provided herein, that an endothelial cell-based biological process that can be modulated by α-defensin is encompassed by the present invention.

The present invention also features a method of inhibiting pathological retinal angiogenesis in a mammal. This is because it has been shown herein for the first time that administration of α-defensin results in about 40% reduction of retinal neovascularization. As described in detail elsewhere herein, α-defensin reduces both the rapid as well as the delayed VEGF-induced increase in endothelial permeability. Moreover, α-defensin inhibits VEGF-induced proliferation of BREC in a dose-dependent manner, as well as capillary tube formation in three-dimensional fibrin-matrices.

Therefore, in one embodiment, the present invention features a method of inhibiting pathological retinal neovascularization in a mammal. The method includes contacting the retinal membrane of a mammal with an α-defensin in order to inhibit retinal neovascularization. Methods of treating a mammal according to the present invention are set forth in detail elsewhere herein.

B. Methods of Identifying Useful Compounds

The present invention further includes a method of identifying a compound that modulates a biological process in a mammal. The method comprises contacting a mammal with a test compound, wherein a higher or lower level of the biological process in a mammal contacted with the test compound compared with the level of the biological process in a second otherwise identical mammal not contacted with the test compound is an indication that the test compound modulates the level of the biological process in the mammal contacted with the compound. If the test compound is additionally found to modulate the interaction between α-defensin and an endothelial cell, then the test compound is thereby identified as a compound that stimulates angiogenesis in a cell.

Methods of identifying an increase or decrease in a biological process that can be modulated using a method or composition of the present invention are set forth in detail elsewhere herein. Additional methods useful for identifying an increase or a decrease in a biological process will be apparent to the skilled artisan in view of the present disclosure, and will therefore not be discussed in detail. Methods for identifying interaction between a polypeptide and a cell, such as between an α-defensin and an endothelial cell, are also well-known in the art, and will not be discussed in detail.

The present invention features a method of identifying a compound that stimulates angiogenesis in a mammal. The method comprises contacting a mammal with a test compound, wherein a higher level of angiogenesis in a mammal contacted with the test compound compared with the level of angiogenesis in a second otherwise identical mammal not contacted with the test compound is an indication that the test compound increases the level of angiogenesis in the mammal contacted with the compound. If the test compound is also found to inhibit the interaction between α-defensin and an endothelial cell, then the test compound is thereby identified as a compound of the present invention that stimulates angiogenesis in a cell.

The invention also includes a method of identifying a compound that inhibits angiogenesis in a mammal. The method comprises contacting a mammal with a test compound, wherein a lower level of angiogenesis in a mammal contacted with the test compound compared with the level of angiogenesis in a second otherwise identical mammal not contacted with the test compound is an indication that the test compound decreases the level of angiogenesis in the mammal contacted with the compound. If the test compound is also found to enhance or stabilize the interaction between α-defensin and an endothelial cell, then the test compound is thereby identified as a compound of the present invention that inhibits angiogenesis in a cell.

Numerous methods of measuring angiogenesis in a mammal are known in the art, and will therefore not be described herein. Briefly, angiogenesis can be measured in a mammal using a method such as, but not limited to, The invention also features methods of modulating other biological processes, diseases, disorders and the like. Other biological processes/conditions that can be modulated by methods and compositions of the present invention include, but are not limited to, vasculogenesis, neovascularization, vasoregulation, thrombosis homeostasis, diabetic retinopathy, arthritis, asthma, lung injury, atherosclerosis, and solid tumors.

Compositions

The invention includes a composition comprising an isolated α-defensin. In one aspect of the invention, the composition comprises a pharmaceutically acceptable carrier.

The compositions can be used to administer α-defensin to a cell, a tissue, or an animal. The compositions are useful to treat a disease, disorder or condition mediated by an endothelial cell such that decreasing or increasing a biological process of an endothelial cell in a tissue or animal is beneficial to the animal. That is, where a disease, disorder or condition in an animal is mediated by or associated with the normal or altered biological activity of an endothelial cell, a composition of the present invention can be used to modulate such activity of an endothelial cell.

For administration to a mammal, a polypeptide can be suspended in any pharmaceutically acceptable carrier, for example, HEPES buffered saline at a pH of about 7.8.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease or condition being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer α-defensin according to the methods of the invention.

Compounds which are identified using any of the methods described herein may be formulated and administered to a mammal for treatment of excessive or insufficient angiogenesis, vasculogenesis, vasoregulation, thrombosis homeostasis, and the like, are now described. As described in detail elsewhere herein, such a compound may be an α-defensin, or alternatively, such a compound may be a non-α-defensin, wherein the compound has been demonstrated by a method set forth herein to modulate the interaction between an α-defensin and an endothelial cell, an endothelial cell and an ECM, an endothelial cell and fibronectin, and the like.

The invention encompasses the preparation and use of pharmaceutical compositions comprising a compound useful for treatment of excessive or insufficient angiogenesis, vasculogenesis, vasoregulation, thrombosis homeostasis, and the like, as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmologically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

V. Kits

The invention includes various kits which comprise a compound, such as an α-defensin or a mixture of α-defensins. Although exemplary kits are described below, the contents of other useful kits will be apparent to the skilled artisan in light of the present disclosure. Each of these kits is included within the invention.

In one aspect, the invention includes a kit for alleviating a disease, disorder or condition mediated by an endothelial cell. The kit is used pursuant to the methods disclosed in the invention. Briefly, the kit may be used to contact an endothelial cell with α-defensin, wherein the action of α-defensin on the endothelial cell mediates a beneficial effect.

The kit further comprises an applicator useful for introducing α-defensin to the endothelial cell. The particular applicator included in the kit will depend on, e.g., the form of α-defensin and/or the composition used to introduce α-defensin to the cell. Such applicators are well-known in the art and may include, among other things, an implant, a syringe, and the like. Moreover, the kit comprises an instructional material for the use of the kit. These instructions simply embody the disclosure provided herein. The kit may also include a pharmaceutically-acceptable carrier. The composition is provided in an appropriate amount as set forth elsewhere herein. Further, the route of administration and the frequency of administration are as previously set forth elsewhere herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

Reagents: α-defensins (human neutrophil peptides 1-3) were isolated from human Neutrophils and from sputum of cystic fibrosis patients and characterized as described by Harwig et al. (1994, Methods Enzymol. 236-:160-172). Three bands of HNP1-3 were detected on SDS-PAGE by western blot and commassie staining. A murine monoclonal antibody against human α-defensin was used. Lipoprotein (a) [Lp(a)] was isolated using lysinesepharose chromatography as described by Bdeir et al. (1999, Blood 94:2007-2019). Recombinant human β-defensins (HBD-2) were also used. VN was purified from human plasma and converted to the multimeric form as described by Chavakis et al. (1998, Blood 91:2305-2312); FBG, FN and sphingosine-1-phosphate were purchased from Sigma (Munich, Germany); monoclonal antibody against β-1 integrin was from DAKO (Hamburg, Germany), cyclic RGDfV peptide was from Bachem (Heidelberg, Germany). Monoclonal antibody against β-1 was also used. Endothelial cell growth serum (ECGS) was from PromoCell (Heidelberg, Germany). Basic fibroblast growth factor (bFGF) and vascular endothelial growth factor (VEGF) were from R&D Systems (Wiesbaden, Germany).

Cell culture: Bovine retinal endothelial cells (BREC) were used and cultivated and human umbilical vein endothelial cells (HUVEC) as described by. All culture media were from Gibco (Eggenstein, Germany).

Cell adhesion assays: Cell adhesion to multiwell plates coated with FN, YN and FBG (and to BSA-coated wells as control) was tested according to previously described protocols (Chavakis et al., 2000, Blood 96:514-522). Briefly, multiwell plates were coated with 5 μg/ml FN, YN or FBG (dissolved in bicarbonate buffer, pH 9.6), respectively, and blocked with 3% (wt/vol) BSA. Confluent BREC or HUVEC were detached with trypsin, which was subsequently neutralized with soybean trypsin inhibitor (Sigma, Germany), were washed in serum-free DMEM and plated onto the precoated wells at 37° C. in the absence or presence of competitors in serum-free DMEM. After an incubation period of 60 mm the wells were washed and the number of adherent cells and the intensity of staining with crystal violet was quantified at 590 nm.

Cell migration assays: Chemotaxis of HUVEC and BREC was tested in modified Boyden chamber assays. Polycarbonate filter membranes (Nucleopore; Whatman, Clifton, N.J.) with 8 μm pore size were coated with FN, VN, FBG or collagen 1(5 μg/ml) in PBS for 16 hours at 4° C. and then washed and air dried before use. After gentle trypsinization (see above), the cells were resuspended in DMEM contains 0.2% (vol/vol) FCS. Each factor was tested in triplicates using 20,000 cells in the upper well, with the test factors in the lower wells. After 3 hours at 37° C., the upper side of the membrane was scraped with a cell scraper to remove non-adherent cells. Membranes were fixed with methanol-acetone (1:1) for 30 mm and stained with crystal violet for another 30 min, then washed in water and fixed between two slides. Adherent cells were counted and a densitometric analysis of the stained spots was made using the Scion image software (NIH, Bethesda, Md.).

Cell proliferation: Endothelial cell proliferation was determined by measuring the incorporation of bromodeoxyuridine (BrdU). Endothelial cells were plated onto 96-well plates and incubated for 12 hours after which the medium was changed to MCDB-131 containing 0.05% FCS. Cells were then incubated for 24 hours in the absence or presence of stimuli or competitors. BrdU was added to the medium during the last 6 hours of incubation. The cells were then fixed and cell proliferation was quantified with a standardized calorimetric immunoassay (Roche Diagnostics, Mannheim, Germany) according to the manufacturer's instructions.

Detection of apoptosis using flow cytometry: Endothelial cell apoptosis was measured as described by Al-Fakhri et al. (2003, Biol. Chem. 384:423-435). HUVEC or vascular smooth muscle cells were cultivated for 16 hours in the absence or presence of stimuli or competitors; thereafter, cells were detached with trypsin (2.5 mg/ml) that was immediately neutralized with soybean trypsin inhibitor. The cells were harvested by pelleting at 500 g/5 mm, washed repeatedly with PBS, pH 7.5, and then resuspended in ice-cold binding buffer (10 mmol/l HEPES/NaOH, pH 7.5, 140 mmol/l NaCl, 2.5 mmol/l $CaCl_2$). The percentage of apoptotic cells was quantified using the Annexin V-FITC kit (Immunotech/Beckman Coulter, Marseille, France). Counterstaining with propidium iodide (red fluorescence) was performed to discriminate between necrotic and apoptotic cells. Briefly, cells were incubated for 10 mm at RT with 0.5 µg/ml FITC-labeled annexin V and 2 µg/ml propidium iodide, and then washed with binding buffer to avoid induction of apoptosis through the staining process. FACS analysis (Epics-XL, Beckman Coulter Electronics, Krefeld, Germany) was immediately carried out using standard protocols. Apoptotic cells were defined as those that exhibited exclusively green fluorescent signals within pre-defined gating criteria of forward and sideward scatter. The maximum rate of apoptosis induction for a 16 hours-cultivation period had been determined in initial experiments.

Capillary tube formation: A protocol described by Koblizek et al. (1998, Curr. Biol. 8:529-532) was modified to use BREC grown on Cytodex-3 microcarriers (Sigma; St. Louis, Mo.) at 37° C. with 5% $CO_2$ in complete MCDB-1 31 medium. Approximately 100 confluent microcarriers coated with BREC were added per well to sterile-filtered solutions containing 1.8 mg/ml fibrinogen in PBS and then α-thrombin (0.65 NIH U/ml) was immediately added for 30 mm to induce fibrin clot formation. Then, 1 ml of medium containing 200 KIU/ml aprotinin alone or together with 0.1% ECGS and in the absence or presence of competitors was added and plates were incubated for an additional 48 hours at 37° C. The number of capillary-like sprouts was evaluated microscopically and was expressed as sprouts/microcarrier.

Chicken chorioallantoic membrane (CAM) angiogenesis assay: The CAM assay was performed to determine the antiangiogenic effect of α-defensin in vivo using a previously described method of Ausprunk et al. (1975, Am. J. Pathol. 79:597-628), with minor modifications. Fertilized chicken eggs were prepared by cutting a window into the shell on day 3 of incubation at 37° C. in a humidified incubator. On day 10, methylcellulose disks saturated with α-defensin (100 µM or 300 µM), or with bFGF (50 ng) as a positive control, or with buffer alone as a negative control were laid onto the egg chorionallantoic membrane. Blood vessel density around (magnification: ×10) or within the disks (magnification: ×16) was evaluated and photographed using a stereomicroscope (Leica, Wetzlar, Germany) on day 13. Five CAMs were analyzed for each test group and the experiments were repeated at least three times.

Example 1

Inhibition of Endothelial Cell Adhesion and Migration by α-defensins

Figure 1B:
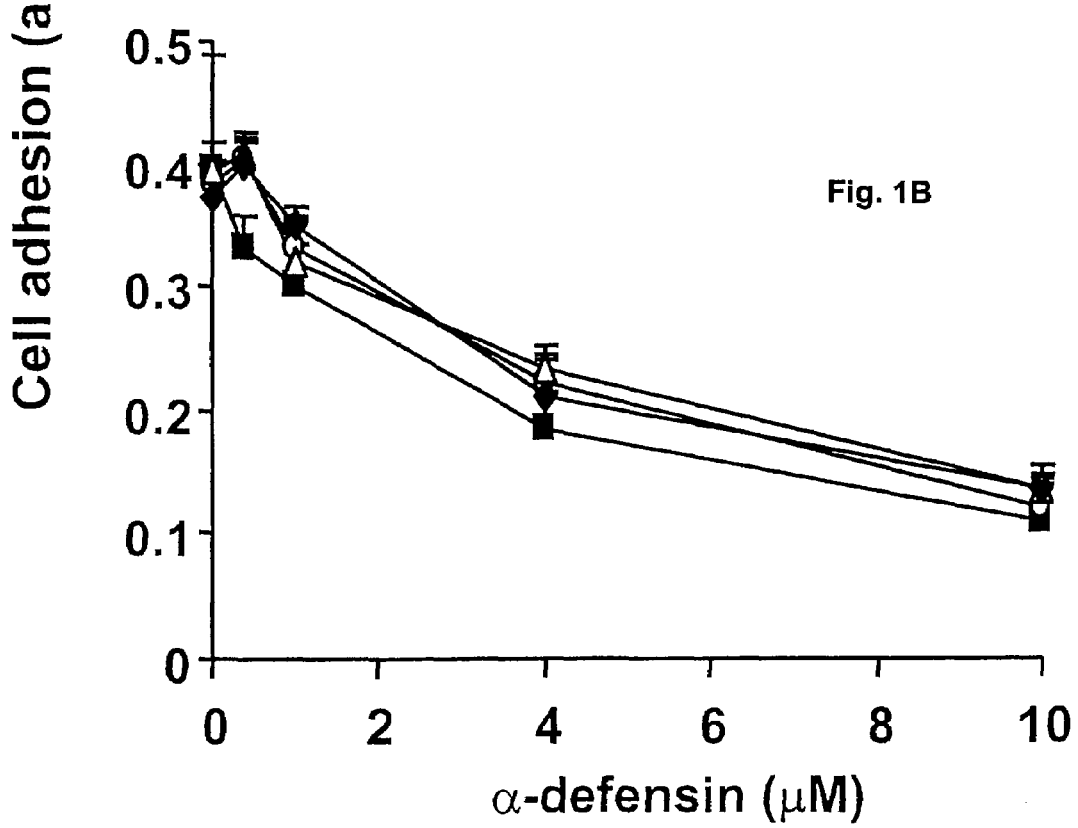
FIG. 1B is a graph depicting the effect of α-defensin on endothelial cell adhesion. Adhesion of HUVEC to immobilized FM (5 μg/ml) is shown alone or in the presence of increasing concentrations of α-defensin, in the absence (filled squares) or presence of 10 nM Lipoprotein A (open circles), 20 nM Lipoprotein A (open triangles) or 50 nM Lipoprotein A (filled diamonds). Cell adhesion is expressed as absorbance at 590 nm. Data are shown as the Mean+/−STD (n=3) of a typical experiment; similar results were obtained in three separate experiments.

Endothelial cells adhere via different integrins to matrix proteins such as FN, FBG, or VN. Whereas endothelial cell adhesion to FBG and VN is predominantly dependent on αv-integrins, β1-integrins mediate adhesion to FN (FIG. 1A). The effect of α-defensins on the adhesion of HUVEC and BREC to these different matrix proteins was investigated. α-defensins specifically blocked endothelial cell adhesion to FN, whereas adhesion to FBG or VN was not affected (FIG. 1A). The anti-adhesive effect of α-defensins was dose-dependent (FIG. 1B), reaching a maximum of ~90% at α-defensin concentration of 10 µM. well within the plasma concentration detected in systemic infection. As α-defensins promote the binding of Lp(a) to FN in the extracellular matrix of vascular cells, the effect of Lp(a) on the antiadhesive activity of α-defensins was tested. Lp(a) did not affect endothelial cell adhesion to any of the substrates directly and the antiadhesive effect of α-defensins on FN-adhesion was not altered in the presence of Lp(a) (FIG. 1B).

α-defensins also specifically reduced the migration of HUVEC towards fibronectin both under control conditions and under stimulation with VEGF, whereas migration towards collagen, VN or FBG was not affected (FIG. 2A). Again, inhibition of HUVEC migration towards FM by α-defensins was dose-dependent (FIG. 2B) and not affected by Lp(a) (not shown). Similar results were observed with BREC. Neither endothelial cell adhesion to FN nor migration towards FN were affected by β-defensins even at the highest concentrations tested (10 µM). These results demonstrate that α-defensins block endothelial cell adhesion and migration in a α5β1-integrin-FN-specific manner.

Example 2

Inhibition of Endothelial Proliferation by α-defensins

Endothelial cell proliferation is stimulated during angiogenesis. Therefore, the influence of α-defensins on HUVEC proliferation was examined by measuring de novo DNA synthesis by measuring the incorporation of BrdU. VEGF and sphingosine-1-phosphate are known activators of endothelial cell proliferation. Both agonists increased DNA synthesis approximately two-fold over a period of 24 hours. HUVEC proliferation was inhibited in the presence of α-defensins in a dose-dependent manner both under control conditions as well as under stimulation with VEGF or sphingosine-1-phosphate (FIG. 3A). To elucidate the mechanism by which α-defensins inhibit proliferation, the induction of apoptosis by α-defensins was examined. α-defensins induced the apoptosis of HUVEC cultivated on FN-coated plates in a dose-dependent manner (FIG. 3B). In contrast, β-defensins did not influence HUVEC proliferation or apoptosis at the same concentrations (FIG. 3B). α-defensins did not affect the proliferation or apoptosis of other cell types tested, such as smooth muscle cells and fibroblasts at these concentrations, nor did Lp(a) affect the anti-proliferative and the pro-apoptotic effect of α-defensin. Together, these studies demonstrate that α-defensins specifically induce apoptosis of endothelial cells and thereby inhibit endothelial cell proliferation.

Example 3

Inhibition of Capillary Sprout Formation by α-defensins

The data set forth herein demonstrate that α-defensins can regulate endothelial cell adhesion, migration and proliferation in vitro, all three of which processes essential for neovascularization. Therefore, the role of α-defensins was examined in a more complex "angiogenesis-resembling" in vitro assay that simulated angiogenesis. Capillary-like tube formation in three-dimensional fibrin gels depends on vascular permeability as well as on the invasive, migratory and proliferative potential of endothelial cells. In this system, α-defensins reduced the number of capillary-like tubes formed during an incubation period of 48 hours in the presence of 0.1% of ECGS. The extent of inhibition was dose-dependent and mirrored the observed in vitro activity; almost complete inhibition of tube formation by α-defensins was observed at concentrations above 5 µM (FIGS. 4A and 4B). Again, β-defensins had no effect on capillary tube formation in this experimental setting.

Example 4

Inhibition of Angiogenesis in the CAM-Assay by α-defensins

Figure 5:
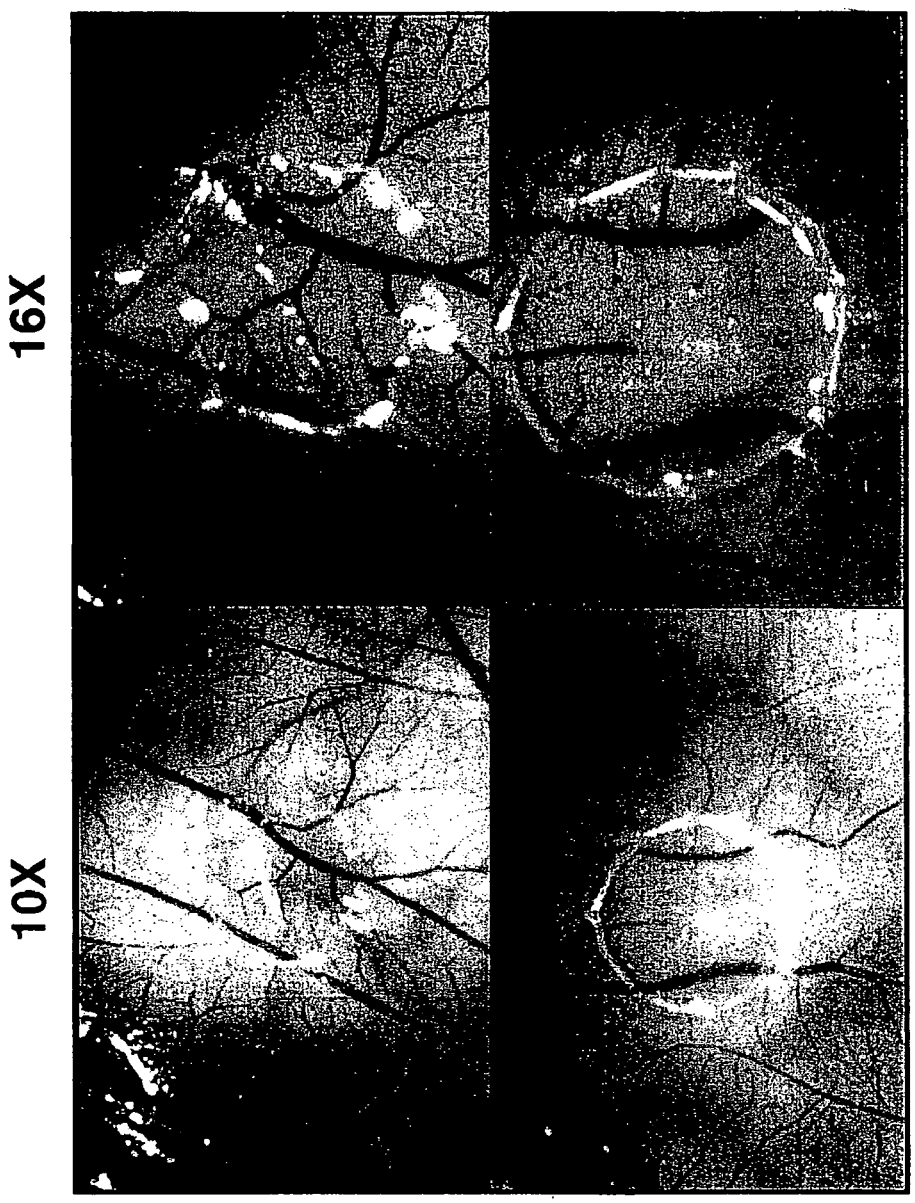
FIG. 5 is a collection of images arranged in a grid to illustrate the inhibition of angiogenesis by α-defensin in the chicken chorioallantoic membrane (CAM)-Assay. Neovascularization in the CAM-Assay was performed as described in the Experimental Examples, in the absence (control) or presence of α-defensin. The upper left panel depicts a 10× magnification of the control assay; the upper right panel depicts a 16× magnification of the control assay; the lower left panel depicts a 10× magnification of an α-defensin-containing assay; and the lower right panel depicts a 16× magnification of an α-defensin-containing assay.
Figure 6A:
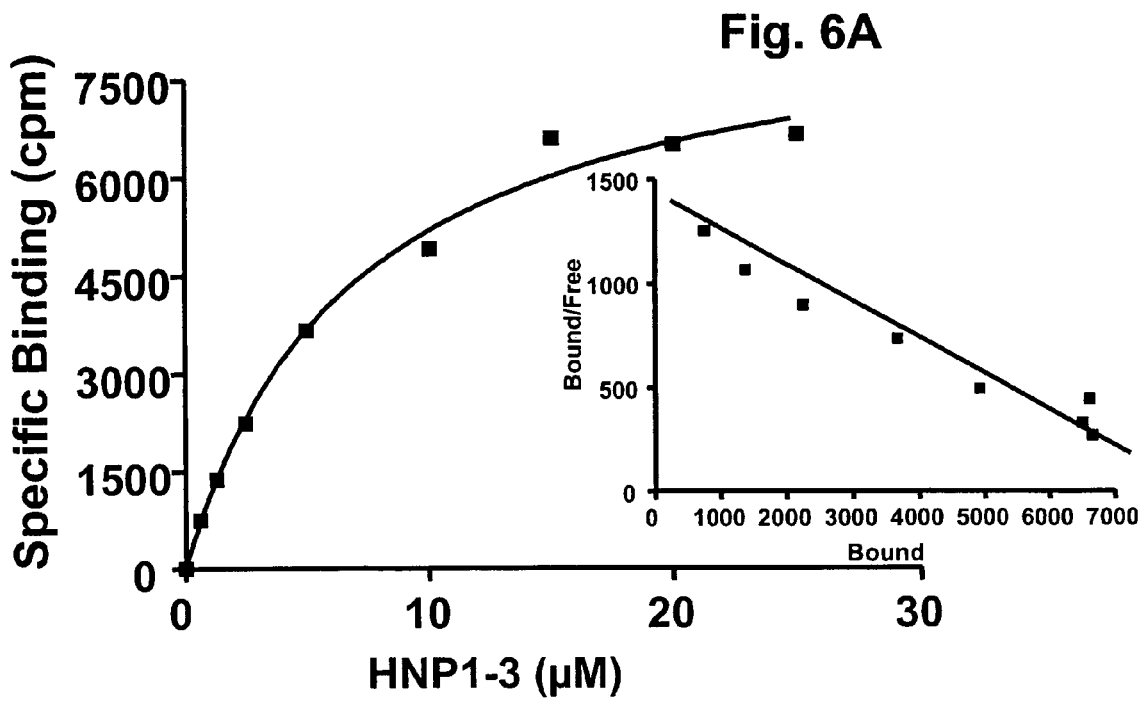
FIG. 6A is a graph depicting the binding of HNPs to α5β1-integrin. $^{125}$I-HNPs in HBS containing 0.1% BSA and 2 mM $MnCl_2$ was added to wells pre-coated with 2.5 μg/ml α5β1 in HBS/2 mM $MnCl_2$ for 1 h at 37° C., washed and the bound radioactivity was counted. Binding to immobilized BSA was subtracted from total binding as a measure of non-specific binding. Results from one experiment, representative of three so performed, is shown. A scatchard plot of the data is shown in the insert.
Figure 6B:
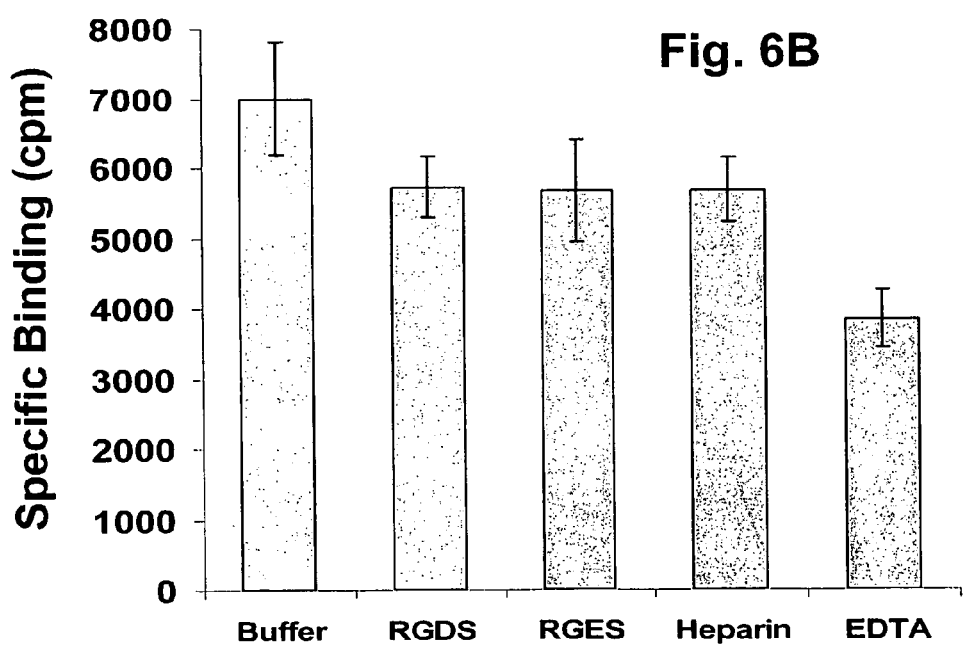
FIG. 6B is a graph depicting specific binding of $^{125}$I-HNPs (1 μM) to immobilized α5β1-integrin in the absence (−) or presence of RGDS or RGES (1 mg/ml), heparin (4 units/ml), or EDTA (10 mM). Binding to immobilized BSA was subtracted from total binding as a measure of non-specific binding.

The anti-angiogenic activity of α-defensins in vivo was investigated using the CAM assay, as described elsewhere herein. On day 13, there was a virtual absence of capillaries at center of the methylcellulose disc and the fragmentation of preexisting small vessels in CAMs exposed to α-defensins, while flanking larger vessels were unaffected (FIG. 5, magnification: left panels, ×10; right panels, ×16). α-defensins inhibited angiogenesis both under control conditions and under stimulation with bFGF. In control experiments, buffer alone had no effect on vessel branching (FIG. 5).

Example 5

Measurement of Angiogenesis in a Mammal

Angiogenesis was measured in a mammal using a MATRIGEL assay (Collaborative Biomedical Products; Bedford, Mass.). Several samples were prepared, including MATRIGEL alone, MATRIGEL containing growth factor bFGF, and MATRIGEL mixed with 1×10$^6$/ml B16/F10 melanoma cells. Samples were injected subcutaneously in both flanks of 8 week-old C57B16 mice. In one flank, the tested compound was added; in the other flank, buffer was used as the control. Five days later, the MATRIGEL pellet was exposed. Blood vessel density around or within the MATRIGEL was quantified.

Angiogenesis was also measured in a mammal using a cornea micropocket assay, as described by Zhou et al. (2004, Cancer Res. 64:4699-4702). Briefly, a corneal micropocket is created on one eye of a 6-week old mouse. A micropellet containing bFGf is implanted, and corneal microvascularization was examined 5 days later (DeLisser et al., 1997, Am. J. Pathol. 151:671-677).

Example 6

Inhibition of Pathological Retinal Neovascularization by α-defensin

The effect of α-defensins on pathological retinal angiogenesis was examined. In vitro, α5β1-integrin-dependent migration of bovine retinal endothelial cells (BREC) to FN, both under control conditions and under stimulation by VEGF, was inhibited specifically by α-defensins. In addition, α-defensins reduced both the rapid (1 h), as well as the delayed VEGF-induced increase in endothelial permeability. Moreover, α-defensins inhibited VEGF-induced proliferation of BREC in a dose-dependent manner, as well as capillary tube formation in three-dimensional fibrin-matrices. In vivo, an upregulation of α5β1-integrin and FN was observed in the mouse model of hypoxia-induced retina angiogenesis, as compared to normal retinas. In this model, administration of α-defensins resulted in about 40% reduction of retinal neovascularization. Accordingly, higher apoptosis was observed in retinas of mice that were treated with α-defensins as compared to control-treated mice. Taken together, these results indicate that α-defensins can inhibit pathological retinal neovascularization in vivo and may provide the platform for developing a clinically feasible and efficient strategy against proliferative retinopathies.

Emerging evidence points to the likelihood that inflammatory changes within the vessel wall regulate the neovascularization that is associated with tumor growth, wound healing and inflammatory diseases such as psoriasis and atherosclerosis. Inflammatory cells such as neutrophils, recruited to the inflamed or injured tissue, can release growth factors as well as proteases capable of modulating tissue structure and promoting angiogenesis. On the other hand, neutrophil-derived elastase can generate the anti-angiogenic factor angiostatin and the net effect of neutrophil products on the angiogenic process is unknown.

In the present application, the effect of α-defensins, the most abundant proteins secreted by activated neutrophils, on angiogenesis and related endothelial cell functions was examined. α-defensins are found in abundance in human atherosclerotic lesions and are known to modify lipoprotein metabolism and inhibit plasminogen activation. It has been demonstrated for the first time herein that α-defensins inhibit the adhesion of endothelial cells to extracellular matrix, block endothelial cell proliferation, and abrogate capillary tube formation.

It has been demonstrated that these alterations in endothelial cell function caused by α-defensins are mediated through an interaction with ECM-associated FN. During angiogenesis, ECM-associated FN is incorporated into an adhesive fibrillar network that regulates diverse endothelial cell functions including growth, differentiation and migration, by transmitting signals to the cells through specific receptors, predominantly α5β1-integrin. For this reason, we tested the hypothesis that the interaction between α-defensins and FN might regulate angiogenesis. In support of this hypothesis, the studies reported here show that: (i) a5β1-integrin-mediated endothelial cell adhesion to and migration towards FN, both under control conditions and under stimulation by vascular endothelial growth factor (VEGF), was specifically inhibited by α-defensins in a dose-dependent manner at concentrations well below those that are known to be cytotoxic to this cell type, whereas adhesion and migration to other ECM proteins, such as vitronectin, collagen or fibrinogen/fibrin was unaffected excluding non-specific cytotoxic effect of defensins. The effect of defensin on these FM-dependent processes was irreversible over the time course studied. (ii) α-defensins completely block VEGF- and sphingosine-1-phosphate-induced proliferation of endothelial cells and induced apoptosis in a dose-dependent manner. (iii) Capillary-like tube formation in three-dimensional fibrin-matrices was also inhibited by α-defensins. (iv) Lastly, α-defensins inhibited neovascularization in the CAM-Assay in vivo.

Although not wishing to be bound by theory, α-defensins may inhibit angiogenesis through several complementary mechanisms in addition to disrupting productive interactions between FN and integrins. For example, α-defensins are among the predominant inhibitors of plasminogen activation at sites of acute inflammation. This may shift the proteolytic balance in and around emerging vascular tissue by decreasing matrix degradation and remodeling. This would attenuate the capacity of endothelial cells to migrate and reorganize into capillary tubes as is required for effective neovascularization. In addition, it was found that α-defensins induce endothelial cell apoptosis and thereby inhibit endothelial cell proliferation. The pro-apoptotic effect of α-defensins may be attributed to their anti-adhesive effect or through an alternative signal-transducing mechanism.

The physiologic relevance and implications of the observed anti-angiogenic function of α-defensins are several. First, one mechanism by which the innate immune system copes with invasive microbes is to invest them in fibrin, which deprives them of nutrition. α-defensins may contribute to this effect by both inhibiting plasminogen activation as well as by inhibiting the formation of new vessels required to supply oxygen and nutrients to rapidly dividing organisms. This initial walling off process may be followed by a period of enhanced neovascularization during the healing phase characterized by rubor and edema. The healing phase may also be mediated in part by other anti-microbial peptides, e.g. cathelcidin peptide LL-37, which is generated by monocytes, NK cells, T-cells, B-cells and epithelial cells and stimulates endothelial cell proliferation and neovascularization via mechanism involving the G-protein coupled formyl peptide receptor-like 1. Thus, the local balance between pro- and anti-angiogenic peptides may serve a regulatory function that contributes to host survival and tissue repair.

Second, the anti-angiogenic properties of α-defensins may extend to several pathophysiological processes as well. For example, in addition to impairing the vascular metabolism of Lp(a) and LDL and inhibiting fibrinolysis, α-defensins may also impede the development of a functional vasa vasorum in atherosclerotic vessels. The hypothesis, that α-defensins are an endogenous modulator of plaque stability angiogenesis requires additional study. The presence of α-defensins in human tumors may serve a salutary function, helping to control tumor angiogenesis and thereby tumor growth.

Other disorders, e.g. ischemia, secondary to vascular occlusion (clot) or disease (atherosclerosis) may result from unimpeded neutrophil activation, local release of α-defensin and failure to attain optimal revascularization. Measures that impede defensin-fibronectin interactions constitute a way to promote natural or therapeutic (e.g. VEGF-) neovascularization.

Taken together, the findings set forth herein suggest that α-defensins are potent regulators of angiogenesis. α-defensins may thus provide a platform for developing a novel class of anti-angiogenesis compounds in cancer and other conditions, e.g. diverse retinopathies or blindness associated with exuberant and pathological vascular growth.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of inhibiting adhesion of an endothelial cell to fibronectin, said method comprising contacting fibronectin with an isolated α-defensin in an amount sufficient to inhibit endothelial cell adhesion to fibronectin, wherein said α-defensin comprises human neutrophil peptide 1 (HNP1), HNP2, HNP3, HNP4, human defensin 5 (HD5), HD6, or any combination thereof, thereby inhibiting adhesion of an endothelial cell to fibronectin.

2. A method of inhibiting migration of an endothelial cell to fibronectin, said method comprising contacting fibronectin with an isolated α-defensin in an amount sufficient to inhibit migration of an endothelial cell to fibronectin, wherein said α-defensin comprises HNP1, HNP2, HNP3, HNP4, HD5, HD6, or any combination thereof thereby inhibiting migration of an endothelial cell to fibronectin.

* * * * *